United States Patent [19]

Eaton et al.

[11] Patent Number: 4,717,657
[45] Date of Patent: Jan. 5, 1988

[54] PREDICTIVE TEST FOR ADVERSE REACTIONS TO IODINATED RADIOGRAPHIC CONTRAST MEDIA

[75] Inventors: Stephen M. Eaton, Hopewell; Horng-Mou Tsay, Kendall Park; James J. Hagan, Holmdel; Frederick J. Yost, Long Valley, all of N.J.

[73] Assignee: E. R. Squibb & Sons, Inc., Princeton, N.J.

[21] Appl. No.: 755,756

[22] Filed: Jul. 17, 1985

[51] Int. Cl.$^4$ .................. C12Q 1/34; C12Q 1/36; C12Q 1/38; C12Q 1/44
[52] U.S. Cl. ........................... 435/18; 435/19; 435/23; 436/539; 436/540; 436/547; 436/821; 436/822
[58] Field of Search .................. 435/18, 19, 23; 486/821

[56] References Cited

FOREIGN PATENT DOCUMENTS 0044127 1/1982 European Pat. Off. .

OTHER PUBLICATIONS

Fareed, J. et al., "Molecular Markers of Contrast Media Induced Adverse Reactions", Scientific Exhibit #613, Radiological Soc. N. Amer. Chi., II; Nov. 13-18, 1983.
Arroyave, C. et al., "Activation of the Alternative Pathway of the Complement System by Radiographic Contrast Media", Journal of Immunology, vol. 117, No. 5, Part 2, pp. 1866-1869.
Hammerschmidt, D. E. et al., "Association of Complement Activation and Elevated Plasma-C5a with Adult Respiratory Distress Syndrome", The Lancet, May 3, 1980.
Siegle, R. L. et al., "In Vitro Complement Consumption by Contrast Media and Analogues: Reactors v. Nonreactors", Investigative Radiology, 1983.
Hakim, R. M. et al., "Complement Activation and Hypersensitivity Reactions to Dialysis Membranes", New England J. Med., 1984, vol. 311, pp. 878-882.
Dawson, P. et al., "Complement Activation and Generation of $C_{3a}$ Anaphylatoxin by Radiological Contrast Agents", Brit. J. Radiol., 1983, vol. 56, pp. 447-448.
VonZabern, I., et al., "Effect of Radiographic Contrast Media on Complement Components C3 and C4: Generation of C3b-Like C3 and C4b-Like C4" J. Immunopharmacology, vol. 5, No. 6, pp. 503-513, 1981.
Lasser, E. C. et al., "Changes in Complement and Coagulation Factors in a Patient Suffering a Severe Anaphylactoid Reaction to Injected Contrast Material: Some Considerations of Pathogenesis", Invest Radiol, 1980, vol 15.
Lasser, E. C. et al., "Prekallikrein-Kallikrein Conversion Rate as a Predictor of Contrast Material Catastrophies", Radiol. 1981, vol. 140, 11-15.
Northcote, D. H. "The Molecular Structure and Shape of Yeast Glycogen", Biochem. J., 1953, vol. 53, pp. 348-352.
Smith, M. C. et al., "Inhibition of Zymosan-Induced Alternative Complement Pathway Activation by Concanavalin A", Infection and Immunity, Dec., 1982, pp. 1279-1284.
Bacon, J. S. D., et al., "The Glucan Components of the Cell Wall of Baker's Yeast (Saccharomyces cerevisiae) Considered in Relation to its Ultrastructure", Biochem. J., 1969, vol. 114, pp. 557-567.
Bellavite, P. et al., "The Measurement of Superoxide Anion Production by Granulocytes in Whole Blood. A Clinical Test for the Evaluation of Phagocyte Function and Serum Opsonic Capacity", Europ. J. of Clin. Invest., vol. 13.
Deby-Dupont, G. et al., "Release of Thromboxane $B_2$ During Adult Respiratory Distress Syndrome and its Inhibition by Non-Steroidal Anti-Inflammatory Substances in Man", Arch. Int. Pharmacodyn. 259, pp. 317-319 (1982).
Larcher, V. F. et al., "Yeast Opsonisation and Complement in Children with Liver Diseased. Analysis of 69 Cases", Pediatric Res. 1983, pp. 296-300.
Radermecker, M. et al., "Increased Complement-Mediated Leukocytic Histamine Release in Atopics", Int. Archs. Allergy Immun., vol. 68, pp. 365-370 (1982).
Herlin, T. et al., "Increased Rate of Opsonization of Zymosan by Serum from Patients with Psoriasis", Arch. Dermatol. Res. (1982), vol. 273, pp. 373-345.
Heberer, M. et al., "Measurement of Chemiluminescence in Freshly Drawn Human Blood", Klin. Wochenschr, 1982, vol. 60, pp. 1443-1448.
Hartung, H. P. et al., "Induction of Thromboxane Release from Macrophages by Anaphylatoxic Peptide C3a of Complement and Synthetic Hexapeptide C3a 72-77", Journal of Immunology, vol. 130, No. 3, pp. 1345-1349.
Hartung, H. P. et al., "Stimulation of Prostaglandino E and Thromboxane Synthesis in Macrophages by Purified C3b", Journal of Immunology, vol. 130, No. 3, pp. 2861-2865.
Holmsen, H. et al., "Differential Energy Requirements for Platelet Responses", Biochem. J., vol. 208, pp. 9-18.
Scheid, C. R., "Direct Effect of Complement Factor C5a on the Contractile State of Isolated Smooth Muscle Cells", Journal of Immunology, vol. 130, No. 5, pp. 1997-1999.
Vercellotti, G. M. et al., "Activation of Plasma Complement by Perfluorocarbon Artificial Blood: Probable Mechanism of Adverse Pulmonary Reactions in Treated Patients and Rationale for Corticosteroid Prophylaxis", Blood, vol. 59, No. 6, 1982.

*Primary Examiner*—Sidney Marantz
*Assistant Examiner*—David A. Saunders
*Attorney, Agent, or Firm*—Lawrence S. Levinson; Donald J. Barrack

[57] ABSTRACT

To determine whether a patient will react adversely when injected intravenously with an iodine-containing contrast media, a sample of the patient's whole blood, whole blood depleted of red blood cells or plasma is treated to activate complement, and the level of at least one product resulting from complement activation is quantified and compared to the level of that product obtained in patients of known reactivity to radiographic contrast media.

19 Claims, No Drawings

PREDICTIVE TEST FOR ADVERSE REACTIONS TO IODINATED RADIOGRAPHIC CONTRAST MEDIA

BACKGROUND OF THE INVENTION

Idiosyncratic reactions occur in 5-8% of all patients receiving iodine-containing radiographic contrast media. Previous reactors to iodine-containing radiographic contrast media, asthmatics and atopic individuals react at twice the frequency of the general population. Fatal reactions have variously been reported at 1 in 40,000 to 1 in 100,000. Atopic patients show no increase in severe or fatal reactions.

Symptoms of adverse iodine-containing radiographic contrast media reactions include: urticaria, nausea, vomiting, diarrhea, hypotension, bronchospasm, laryngeal edema, motor convulsions and myocardial irregularities. Reactions have been classified as mild: requiring no intervention; moderate: responding to immediate treatment; and severe: requiring extensive treatment.

Complement activation by iodine-containing radiographic contrast media has been widely reported to occur in vivo and in vitro. While complement activation by iodine-containing radiographic contrast media is well accepted, the literature is contradictory with respect to the exact sequence of the cascade. Activation of the alternate pathway has been implicated by some, who later reported non-sequential activation. Others showed consumption of classical pathway components and decreased mean levels of the $C_1$ esterase inhibitor in serious reactors. More recently, still others demonstrated transient complement consumption after iodine-containing radiographic contrast media administration.

Alternate complement pathway activation forms the $C_3$ convertase which produces the anaphylatoxic peptides $C_{3a}$ and $C_{3b}$. They trigger separate platelet receptors, which cause release of the alpha granule constituents: platelet factor 4 (PF4), $\beta$-thromboglobulin (BTG), fibrinogen; the dense granule constituents: $Ca++$, serotonin, ADP, ATP and synthesis of arachidonic acid metabolites.

Addition of $C_{3b}$ to the $C_3$ convertase forms the $C_5$ convertase. This enzyme produces $C_{5a}$, an anaphylatoxic peptide which stimulates smooth muscle contraction. Assembly of the terminal lytic complex ($C_{5-9}$) induces arachidonic acid release, PGE2 (prostaglandin $E_2$) and $TxB_2$ (thromboxane $B_2$) synthesis in white cells.

Most attempts to predetermine iodine-containing radiographic contrast media reactions have relied on analysis of circulating levels of serum components. Some claimed that high prekallikrein conversion rates correlated with patient susceptibility to iodine-containing radiographic contrast media-induced reactions. Others have suggested pretesting for components of the kinin, fibrinolytic, complement, coagulation, arachidonic acid and vasoactive amine systems which might define the serum profile of potential reactors.

BRIEF DESCRIPTION OF THE INVENTION

It is an object of this invention to predict which patients are at risk of experiencing an idiosyncratic reaction to an iodine-containing radiographic contrast media.

It is a further object of this invention to reduce the risk to a patient of experiencing an idiosyncratic reaction to an iodine-containing radiographic contrast media, particularly a severe idiosyncratic reaction.

It is a still further object of this invention to provide a test useful for predicting idiosyncratic reactions to iodine-containing radiographic contrast media that is adaptable for use as a routine screening technique.

These, and other objects that will be apparent to the practitioner of this invention, are achieved by the in vitro predictive test described herein. Complement activation of a sample of a patient's whole blood, whole blood depleted of red blood cells or plasma can be accomplished using a complement activator other than radiographic contrast media (referred to hereinafter as a "non-radiographic contrast media complement activator"), and the level of complement activation can be used to predict whether the patient will react adversely when injected intravenously with iodine-containing radiographic contrast media.

DETAILED DESCRIPTION OF THE INVENTION

To ascertain whether a patient will react adversely when injected intravenously with iodine-containing radiographic contrast media, a sample of the patient's whole blood, whole blood depleted of red blood cells or plasma (referred to hereinafter as "the patient's sample") is treated with a non-radiographic contrast media complement activator. Analytes formed during treatment with complement activators are measured using conventional methodology. The level of the various analytes is predictive of whether a patient will have an adverse reaction to iodine-containing radiographic contrast media.

The test of this invention utilizes a sample of the patient's whole blood, whole blood depleted of red blood cells or plasma. If whole blood depleted of red blood cells or plasma are to be used, it will be necessary to first deplete a whole blood sample of red blood cells (leaving white blood cells/platelets in plasma). The plasma containing white blood cells/platelets can be further depleted of white blood cells/platelets.

There are many separation schemes for removing red blood cells from whole blood (leaving white blood cells/platelets in plasma) known to those skilled in the art, among which are sedimentation over density gradients, automated cell sorting systems and centrifugation. The preferred method is centrifugation. Centrifugation will preferably be carried out above 50 $\times$g, and most preferably between about 75 and 150 $\times$g. Centrifiguation time will preferably be at least about 5 minutes and most preferably be between 10 and 15 minutes. The temperature at which the centrifugation is carried out will preferably be above about 15° C. and most preferably be about 20° C. The centrifugation procedure separates the red blood cells from the blood plasma containing white blood cells/platelets.

There are many separation schemes for depleting plasma of white blood cells/platelets known to those skilled in the art, among which are sedimentation over density gradients, automated cell sorting systems, filtration and centrifugation. The preferred method is centrifugation. Centrifugation will preferably be carried out above 1000 $\times$g, and most preferably between about 2000 $\times$g and 3000 $\times$g. Centrifugation time will preferably be at least about 5 minutes and most preferably be between 10 and 15 minutes. The temperature at which the centrifugation is carried out will preferably be above about 15° C. and most preferably be about 20° C.

The centrifugation procedure depletes the blood plasma of white blood cells/platelets.

Sampling of a patient's whole blood (whether for complement activation of that whole blood or for separation into its various components) can be accomplished using conventional technology. Preferably, an anticoagulant is first added to the sample. Citrate salts can be used as anticoagulants; the concentration of citrate in the sample will preferably be about 0.01 to 0.2M.

The whole blood, whole blood depleted of red blood cells or plasma sample is combined with a non-radiographic contrast media complement activator. Exemplary complement activators are zymosan, anti-normal human serum, glucan, carrageenan, protein A, lipopolysaccharide, endotoxin, inulin, dextran sulfate and other polyions. Zymosan is the preferred complement activator. The complement activator will be diluted with an aqueous blood-compatible solvent before addition to the patient's sample. Where zymosan is used as the complement activator, it can be diluted with normal saline. The concentration of zymosan in saline will be about 0.25 to 6.25 mg/ml, preferably 1.25 mg/ml.

The zymosan solution may be diluted with the patient's sample from 1:0.1 to 1:10. Preferably the zymosan solution will be diluted 1:2 with the patient's sample so that the final solution is 0.625 mg zymosan/ml.

The following Table I presents desired ranges for the concentration of various complement activators in an aqueous blood compatible solvent before its addition to the patient's sample.

TABLE I

DILUTION OF COMPLEMENT ACTIVATOR IN AQUEOUS BLOOD-COMPATIBLE SOLVENT

| Activator | Range | Preferred |
|---|---|---|
| anti-normal human serum mg/ml | 0.01–1.0 | 0.05 |
| glucan mg/ml | 0.1–2.5 | 1.25 |
| carrageenan mg/ml | 0.02–2.0 | 0.125 |
| protein A μg/ml | 0.002–0.2 | 0.01 |
| endotoxin eu/ml | 2.0–100.0 | 10.00 |
| inulin mg/ml | 0.250–2.5 | 1.25 |
| dextran sulfate mg/ml | 0.002–0.2 | 0.01 |
| lipopolysaccharide μg/ml | 1.0–50.0 | 10.0 |

In general, irrespective of which complement activator is used, the activator will be diluted with the patient's sample from 1:0.1 to 1:10, preferably about 1:2.

The patient's sample and complement activator are preferably combined and incubated at a temperature above 22° C., most preferably about 37° C. Whole blood, whole blood depleted of red blood cells and plasma have constituents which are energy-requiring, and at lower temperatures, it is found that analyte production is substantially reduced. Preferably, the period of time allowed for complement activation will be at least about 15 minutes, most preferably at least about 30 minutes, and preferably not exceeding about one hour.

Following incubation, the mixture of patient's sample and complement activator can be subjected to a separation process using art-recognized techniques. In the case of whole blood, the separation procedure separates blood plasma from blood cells and insoluble complement activator. In the case of whole blood depleted of red blood cells, the separation procedure separates the plasma containing the analytes from the white blood cells/platelets and insoluble complement activator. In the case of plasma, the separation procedure can be used to separate the plasma from insoluble complement activator. The component to be measured should be transferred to a clean test tube or stored (at about −10° C. to −70° C.) for later use.

Centrifugation is the preferred separation technique and will preferably be carried out above 1000 ×g, and most preferably between about 2000 ×g and 3000 ×g. Centrifugation time will preferably be at least about 5 minutes and most preferably be between about 10 and 15 minutes. The temperature at which the centrifugation is carried out will preferably be above about 0° C. and most preferably be about 6° C.

Analytes that can be quantitated in complement activated patient samples and used to predict a patient's adverse reaction to iodine-containing radiographic contrast media include: $C_{3a}$, arachidonic acid metabolites (e.g., thromboxane $B_2$), platelet factor 4, $\beta$-thromboglobulin, serotonin, $Ca++$, ATP, $\beta$-glucuronidase and lysozyme. The quantification of these plasma and blood cell components can be accomplished using methodology known to those of ordinary skill in the art, e.g., radioimmunoassay, non-isotopic immunoassay, affinity immunoassay, high pressure liquid chromatography and the like.

The following example is a specific embodiment of this invention.

EXAMPLE

Preparation of Activated Plasma

Whole blood samples were drawn into citrated plastic syringes. The syringes contained 0.5 ml of 0.16 M citrate and were calibrated to draw 4.5 ml of blood.

Citrated whole blood sample (5.0 ml) and 5.0 ml of a 1.25 mg/ml zymosan solution in normal saline were combined, mixed and incubated at 37° C. for 30 minutes. Following incubation, the mixture of whole blood sample and zymosan was centrifuged to separate the plasma. Centrifugation was carried out at 3000 ×g for 10 minutes at 6° C. The plasma was tranferred to a clean test tube and analyzed for mediator levels.

The whole blood samples used were taken from patients who were either non-reactors to iodinated radiographic contrast media or *mild* reactors to iodinated radiographic contrast media.

Measurement of Complement Activation Products

Plasma from zymosan-activated whole blood (165 samples) was analyzed for platelet factor 4 using Abbott Diagnostic Company's platelet factor 4 radioimmunoassay kit. The plasma was diluted 1:20 in the diluent provided by the kit, and the remainder of the kit directions were followed. The values obtained for the samples were corrected for dilution and expressed in units of ng/ml plasma. Values for 165 samples from patients of known reactivity to iodine-containing radiographic contrast media were accumulated, and a cutoff of 400 ng/ml plasma applied to separate test positives and negatives; the results are shown in Table II.

Plasma from zymosan-activated whole blood (196 samples) was analyzed for thromboxane $B_2$ using a radioimmunoassay. Antibody against thromboxane $B_2$ was raised in rabbits by injecting thromboxane $B_2$ coupled to bovine serum albumin in the presence of complete Freund's adjuvant. Blood was collected from the rabbits over several months until a serum titre of anti-thromboxane antibody appropriate for radioimmunoassay was obtained. Thromboxane $B_2$-histamine was labeled with $^{125}I$ by a conventional technique and a competition-type radioimmunoassay was developed using polyethylene glycol/goat anti-rabbit immunoglobulin G as the separant for bound versus free $^{125}$I-thromboxane B$_2$-histamine.

Plasma samples were diluted 1:20 in the radioimmunoassay buffer (1 mg/ml bovine serum albumin, 1 mg/ml sodium azide, 0.9% sodium chloride in 0.05 M tris/acetate pH 7.4) and values were obtained from a thromboxane B$_2$ standard curve. The values obtained for the samples were corrected for dilution and expressed in units of pg/ml plasma. Values for 196 samples from patients of known reactivity to iodine-containing radiographic contrast media were accumulated, and a cutoff of 4000 pg/ml plasma applied to separate test positives and negatives; the results are shown in Table II.

Plasma from zymosan-activated whole blood (139 samples) was analyzed for C$_{3a}$ using Upjohn Diagnostic Company's C$_{3a}$ radioimmunoassay kit. The plasma was precipitated using the provided reagent, diluted 1:20 in 1% porcine skin gelatin in 0.05M potassium phosphate-hydrogen chloride, pH 7.3, and the remainder of the kit directions were followed. The values obtained for the samples were corrected for dilution and expressed in units of ng/0.05 ml plasma. Values for 139 samples from patients of known reactivity to iodine-containing radiographic contrast media were accumulated, and a cutoff of 100 ng/0.05 ml plasma applied to separate test positives and negatives; the results are shown in Table II.

TABLE II

| | Sensitivity and Specificity of Tests | | | | | |
|---|---|---|---|---|---|---|
| Test | Total Samples | TP | TN | FP | FN | % Sensitivity | % Specificity |
| PF4 | 165 | 5 | 119 | 40 | 1 | 83 | 75 |
| TxB$_2$ | 196 | 6 | 136 | 52 | 2 | 75 | 72 |
| C$_{3a}$ | 139 | 5 | 89 | 43 | 2 | 71 | 67 |

TP — true positive: clinically positive samples which tested positive
FP — false positive: clinically negative samples which tested positive
TN — true negative: clinically negative samples which tested negative
FN — false negative: clinically positive samples which tested negative
Sensitivity = TP/TP + FN
Specificity = TN/TN + FP The thromboxane B$_2$, platelet factor 4 and C$_{3a}$ values were subjected to a statistical analysis using the Wilcoxon-Mann-Whitney rank sum test. A significant difference ($p<0.05$) was found between non-reacting patients and patients reacting to iodine-containing radiographic contrast media for platelet factor 4 and thromboxane B$_2$. The results of the statistical analysis are shown in Table III

TABLE III

| Wilcoxon-Mann-Whitney Bank Sum Test | | | | |
|---|---|---|---|---|
| analyte | n | sum of scores | mean score | significance |
| PF4 | 159 | 12822 | 81.15 | 0.0313 |
| | 6 | 709 | 118.00 | |
| TxB$_2$ | 188 | 18062 | 96.59 | 0.0459 |
| | 8 | 1048 | 131.00 | |
| C$_{3a}$ | 132 | 8979 | 68.55 | 0.1135 |
| | 7 | 611 | 87.36 | | n - the number of samples tested, the larger number for each test is non-reactors, the smaller number is reactors
significance - the p value for a one-tailed test Combination of analytes predicted reactors to iodine-containing radiographic contrast media with increased specificity above single test results. The combination of thromboxane B$_2$ and platelet factor 4 where both analytes were above the cutoffs resulted in improved specificity and no loss of sensitivity (Table III). Table IV also shows that combinations of analytes where either value was above the cutoff increased specificity but lowered sensitivity.

TABLE IV

| Sensitivity and Specificity of Combination of Tests | | | | | | |
|---|---|---|---|---|---|---|
| Test | Samples | TP | TN | FP | FN | Sensitivity | Specificity |
| TxB$_2$/PF4[1] | 164 | 5 | 141 | 17 | 1 | 83 | 89 |
| TxB$_2$/PF4[2] | 164 | 5 | 92 | 66 | 1 | 58 | 89 |

[1] both analytes greater than their cutoffs
[2] either analyte greater than their cutoff Other analytes have been quantitated in complement activated patient samples such as beta-thromboglobulin, serotonin and calcium. These analytes along with C$_{3a}$ have not been shown to be statistically capable of predicting mild adverse reactions to iodine-containing radiographic contrast media. It is believed, however, that these analytes will be statistically capable of predicting moderate and severe adverse reactions to radiographic contrast media.

What is claimed is:

1. A predictive test for determining whether a patient will react adversely when injected intravenously with iodine-containing contrast media comprising activating complement in a sample of the patient's whole blood, whole blood depleted of red blood cells or plasma using a non-radiographic media complement activator, quantitating the level of at least one product resulting from complement activation and comparing the level of that product to the level obtained in patients of known reactivity to radiographic contrast media.

2. A predictive test in accordance with claim 1 wherein the non-radiographic contrast media complement activator is zymosan.

3. A predictive test in accordance with claim 1 comprising:
   (i) combining a sample of the patient's whole blood with a non-radiographic contrast media complement activator and incubating the sample of whole blood to activate complement;
   (ii) separating the plasma from blood cells;
   (iii) assaying the plasma to determine the level of at least one product resulting from complement activation; and
   (iv) comparing the level of at least one complement activation product in the patient's plasma to the level of that product obtained by carrying out steps (i), (ii), and (iii) using whole blood samples of patients with known reactivity to iodine-containing radiographic contrast media.

4. A predictive test in accordance with claim 3 wherein the non-radiographic contrast media complement activator is zymosan, anti-normal human serum, glucan, carrageenan, protein A, lipopolysaccharide, endotoxin, inulin, or dextran sulfate.

5. A predictive test in accordance with claim 3 wherein the non-radiographic contrast media complement activator is zymosan.

6. A predictive test in accordance with claim 3 wherein the plasma is assayed to determine the level of platelet factor 4.

7. A predictive test in accordance with claim 3 wherein the plasma is assayed to determine the level of thromboxane B$_2$.

8. A predictive test in accordance with claim 3 wherein plasma is separated from blood cells by centrifugation.

9. A predictive test in accordance with claim 1 comprising:
   (i) combining a sample of the patient's whole blood depleted of red blood cells with a non-radiographic contrast media complement activator and incubating the sample of whole blood depleted of red blood cells to activate complement;
   (ii) separating the plasma from the white blood cells/platelets;
   (iii) assaying the plasma to determine the level of at least one analyte resulting from complement activation; and
   (iv) comparing the level of at least one analyte resulting from complement activation to the level of that analyte obtained by carrying out steps (i), (ii) and (iii) using samples of whole blood depleted of red blood cells from patients with known reactivity to iodine-containing radiographic contrast media.

10. A predictive test in accordance with claim 9 wherein the non-radiographic contrast media complement activator is zymosan, antinormal human serum, glucan, carrageenan, protein A, lipopolysaccharide, endotoxin, inulin, or dextran sulfate.

11. A predictive test in accordance with claim 9 wherein the non-radiographic contrast media complement activator is zymosan.

12. A predictive test in accordance with claim 9 wherein the plasma containing the analytes is assayed to determine the level of platelet factor 4.

13. A predictive test in accordance with claim 9 wherein the plasma containing the analytes is assayed to determine the level of thromboxane $B_2$.

14. A predictive test in accordance with claim 9 wherein plasma is separated from white blood cells/platelets by centrifugation.

15. A predictive test in accordance with claim 1 comprising:
   (i) combining a sample of the patient's plasma with a non-radiographic contrast media complement activator and incubating the sample of plasma to activate complement;
   (ii) assaying the plasma to determine the level of at least one product resulting from complement activation; and
   (iii) comparing the level of at least one complement activation product in the patient's plasma to the level of that product obtained by carrying out steps (i) and (ii) using plasma samples of patients with known reactivity to iodine-containing radiographic contrast media.

16. A predictive test in accordance with claim 15 wherein the non-radiographic contrast media complement activator is zymosan, anti-normal human serum, glucan, carrageenan, protein A, lipopolysaccharide, endotoxin, inulin, or dextran sulfate.

17. A predictive test in accordance with claim 15 wherein the non-radiographic contrast media complement activator is zymosan.

18. A predictive test in accordance with claim 17 wherein plasma and zymosan are separated prior to assaying the plasma.

19. A predictive test in accordance with claim 18 wherein plasma and zymosan are separated by centrifugation.

* * * * *